US00PP20450P3

(12) United States Plant Patent
Moore

(10) Patent No.: US PP20,450 P3
(45) Date of Patent: Nov. 3, 2009

(54) FLORIBUNDA ROSE PLANT NAMED 'MORABUNDANT'

(50) Latin Name: *Rosa Floribunda*
Varietal Denomination: MORabundant

(75) Inventor: Ralph S. Moore, Visalia, CA (US)

(73) Assignee: Cottage Hill Nursery, Inc., Irvington, AL (US)

( * ) Notice: Subject to any disclaimer, the term of this patent is extended or adjusted under 35 U.S.C. 154(b) by 114 days.

(21) Appl. No.: 11/888,874

(22) Filed: Aug. 3, 2007

(65) Prior Publication Data

US 2009/0038037 P1 Feb. 5, 2009

(51) Int. Cl.
*A01H 5/00* (2006.01)

(52) U.S. Cl. ..... Plt./148

(58) Field of Classification Search ..... Plt./148, Plt./149

See application file for complete search history.

*Primary Examiner*—Kent L Bell

(57) ABSTRACT

A new and distinct cultivar of rose plant of the floribunda class, of hardy, sturdy, bushy, much branched habit substantially as illustrated and described, characterized by buds and flowers, basically pink, the bud being pointed in the early stage, opening from light pink center to medium pink on outer petals, with the open flower being double and rounded with 40 or more petals; and further characterized by a plant of compact, vigorous, upright shape with main stems and shoots of less than average thorniness, the said plant being easy to propagate from soft-wood cuttings with an abundance of medium, semi-glossy foliage, the flowers being usually borne in medium clusters on medium length stems.

2 Drawing Sheets

Classification: The present invention relates to a new *Rosa* Floribunda plant (*Rosa* spp.).

Variety denomination: The new plant has the varietal denomination 'MORabundant'.

BACKGROUND OF THE INVENTION

This new and distinct cultivar of floribunda rose was originated by Ralph Moore, located at Visalia, Calif., as a result of a cross between 'MORdora' ('Sequoia Ruby', miniature rose climber) as the seed parent and "seedling" ('Golden Gardens'×'Strawberry Ice') as the pollen parent. The following description is of 3 to 4 year-old rose plants of the new variety grown outdoors in Visalia, Calif. in the month of April, 2009. Phenotypic expression may vary with environmental, cultural and climatic conditions, as well as differences in conditions of light and soil.

SUMMARY OF THE INVENTION

The present invention relates to a new and distinct cultivar of hardy, bush type rose plant of the floribunda class. The cultivar is primarily characterized as to novelty by its pink color and double flowers. The cultivar is further characterized by: an abundance of bloom, with flowers usually borne in clusters (sometimes singly) to a stem; slight fragrance; a plant of vigorous, rounded to compact, bushy growth shape, with semi-glossy foliage with elliptical leaflets; the buds and flowers open from light pink from center to medium pink outside tip petals and medium pink on reverse side of petal blooms; a plant which grows and blooms satisfactorily both in greenhouse and outdoors; with repeat bloom, is good for growing in pots, and provides excellent garden decoration as well as cut flowers.

The new cultivar has been successfully asexually reproduced in Visalia, Calif. by budding as well as by cuttings; the reproductions have run true in all respects. The photograph illustrates the cultivar including the foliage, buds and flowers.

BRIEF DESCRIPTION OF THE DRAWINGS

Plant part coloration illustrated is as true as reasonably possible to attain in photographic illustrations of this type. The accompanying photographs illustrate specimens of the new variety and show the flowering thereof from bud to full bloom.

DETAILED BOTANICAL DESCRIPTION OF THE PLANT

Figure 1:
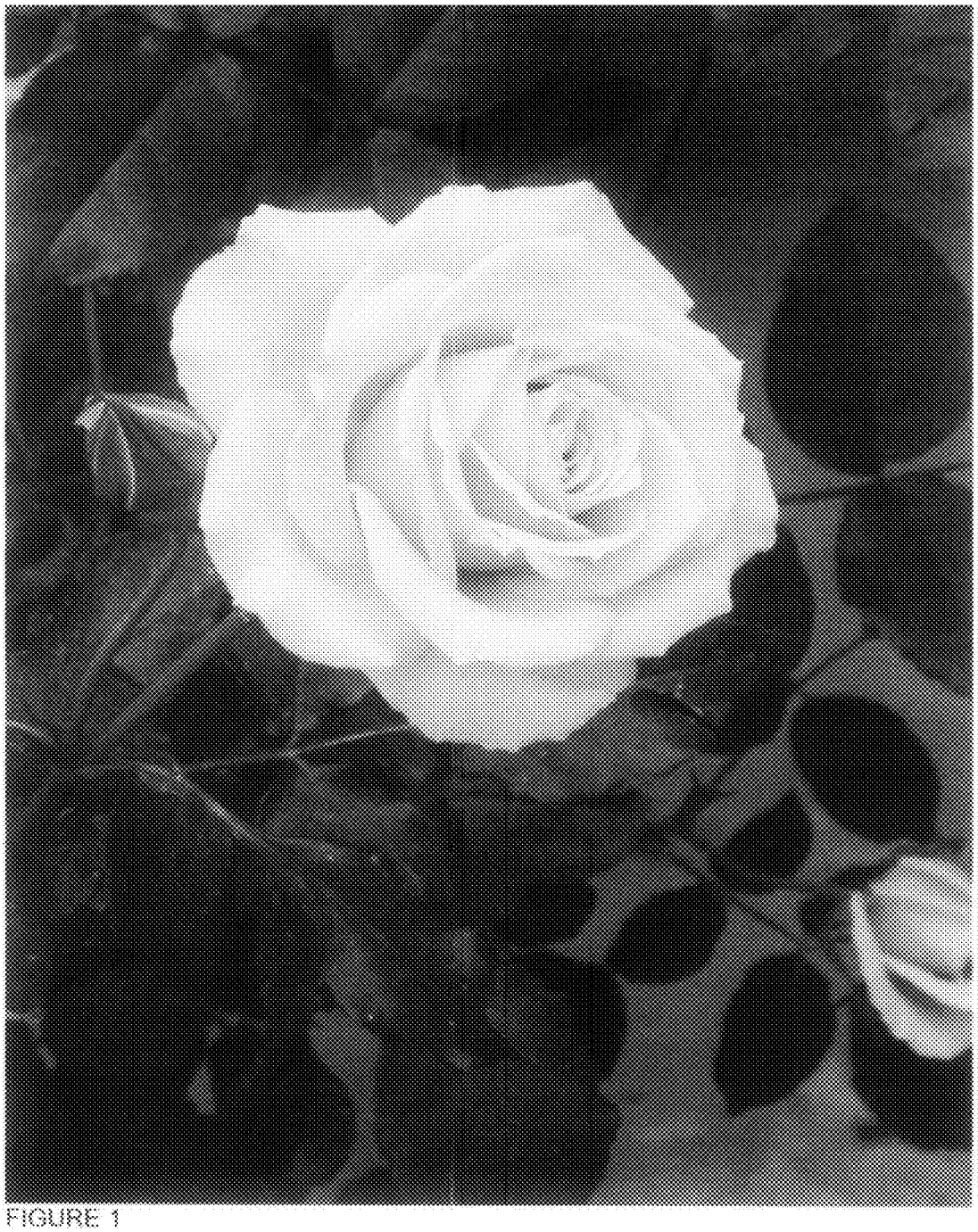
FIG. 1. shows open flower with buds and foliage.
Figure 2:
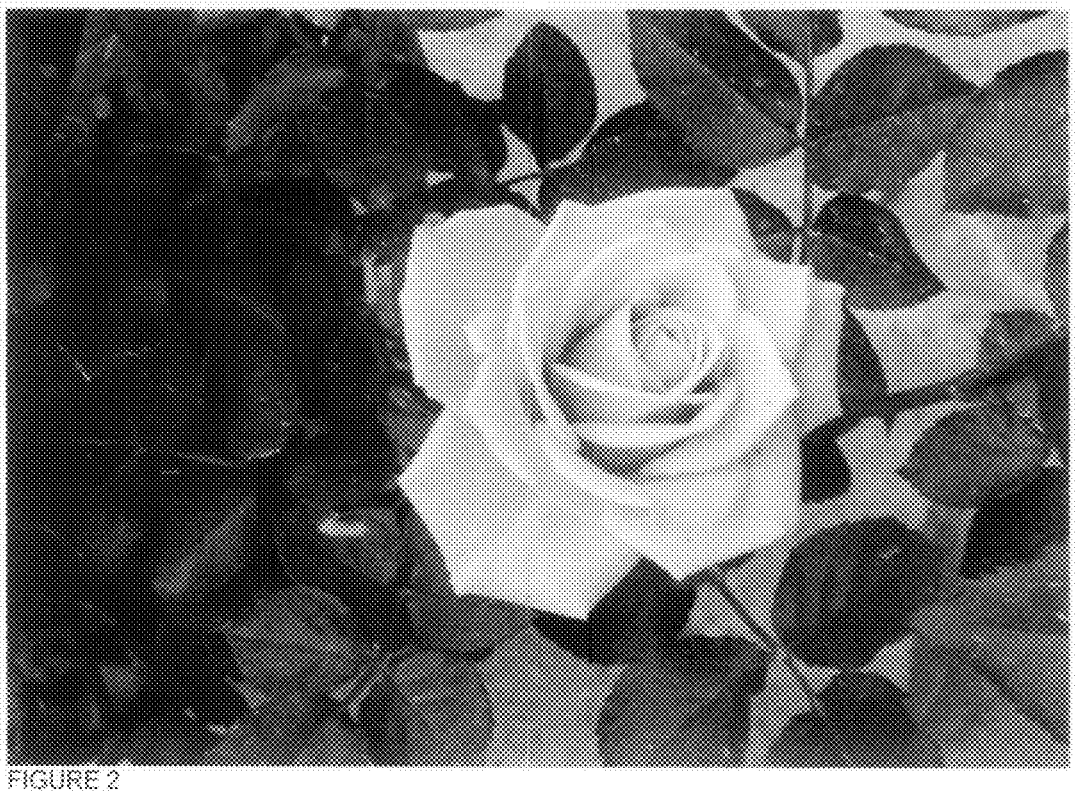
FIG. 2. shows open flower and foliage.
Figure 3:
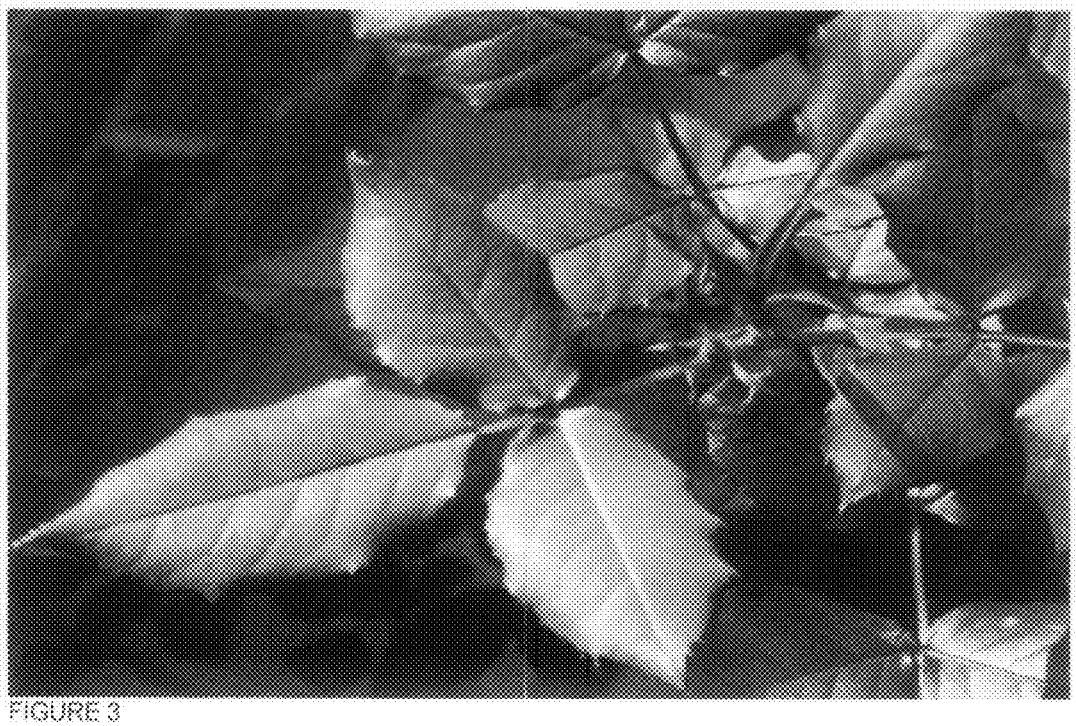
FIG. 3. shows canes and foliage.

Referring now specifically to the new and distinct cultivar of floribunda rose plant, the following is a detailed description thereof in outline; all major color plate identifications being by reference to The R. H. S. Colour Chart (Royal Horticultural Society) except where common terms of color definition are employed.

Flower

The new variety usually bears its flowers in clusters, but also bears singly. Flowers are borne on strong medium stems (about 2.3 to about 27 cm). Outdoors, the plant blooms abundantly and nearly continuously during the growing season. The flowers have a slight old rose fragrance.

Bud

The peduncle is about 5.0 to about 9.0 cm. in length, of average to heavy caliper (about 0.02 to about 0.05 cm. in diameter) and usually erect and somewhat stiff. It is entirely smooth, without stipitate glands, hairs, or prickles. Peduncle color is between 146B and 146C sometimes very lightly suffused, especially on the side exposed to the sun, with near 182A.

Before the calyx breaks, the bud is about 1.2 to about 1.5 cm. In diameter at the widest point, about 2.9 to about 3.4 cm. in length, and globular to somewhat ovoid in shape. The surface of the bud bears some foliaceous appendages, usually with stout somewhat cut foliaceous parts extending beyond the tip of the bud about 0.05 cm or more of its length. Bud color Is between 146B and 146C.

The sepals are about 2.8 to about 3.1 cm. in length and about 1.1 to about 1.2 cm. in width at the widest point. The outer surface color of the sepal is between 146B and 146C. The inner surface color the sepal is between 147C and 146B and covered with fine wooly tomemtum; sepal margins are lined with many stipitate glands and hairs.

As the petals open (after the calyx breaks), the bud is about 2.0 to about 3.0 cm. in diameter at the widest point, about 2.5 to about 3.2 cm. in length, and very globular in form. The color of the under surfaces of the newly opened petals is between 54A and 55C sometimes with pigmentation as dark as between 59C mostly toward the edge of the petal. At the point where the petal attaches, there is a moderately small zone between 4B and 2C. The color of the upper surfaces of the newly opened petals is between 56B and 56A. At the point where the petal attaches, there is a moderately small zone between 4B and 2C.

Bloom

When fully open, the bloom ranges from about 8.5 to about 9.5 cm. in diameter.

Petalage is very double with about 40 to 45 petals and about 3 to 5 petaloids irregularly arranged.

When partially open, the bloom form is high centered to somewhat globular, and the petals are moderately tightly spiraled to slightly cupped with petal edges moderately reflexed outward.

When fully open, the bloom form is more cupped, and the petals are loosely cupped with petal edges moderately reflexed outward.

Petals:

The substance of the petals is of medium thickness, with upper surfaces satiny and shiny and under surfaces is satiny and shiny.

The outer petals are broadly obovate to round in shape with rounded apices and sometimes notched with one notch.

The inner petals are nearly round to moderately obovate in shape with rounded apices and sometimes notched with one notch.

The petals are about 3.5 to about 4.0 cm. in length and about 3.0 to about 4.5 cm. in width at the widest point.

Petal margins are entire to sometimes moderately sinuate especially on the outermost petals edges.

Newly Opened Flowers

The under surface color of the outer petals in between 56B and 56A. At the point where the petal attaches, there is a moderately small zone of between 2C and 2B.

The upper surface color of the outer petals is irregularly shaded with as light as between 56A and 56B.

At the point where the petal attaches, there is a moderately small zone of between 2D and 2C.

The under surface color the intermediate and inner petals is between 56D and 56C.

The upper surface color of the intermediate and inner petals in between 56C and 56A.

The general tonality of the newly open flower is between 56D and 56A.

Three-Day Old Flower

The under surface color of the outer petals is between 56B and 56A. At the point where the petal attaches, there is a moderately small zone of between 2C and 2B.

The upper surface color of the outer petals is irregularly shaded with as light as between 56A and 56C to as dark as between 54C and 54B. At the point where the petal attaches, there is a moderately small zone of between 2D and 2C.

The under surface color of the intermediate and inner petals is between 56D and 56C.

The upper surface color of the intermediate and inner petals is irregularly shaded with as light as between 56D and 56C to as dark as between 56C and 56B.

The general tonality of the three-day-old flower is irregularly shaded with as light as between 56C and 56D to as dark as between 56A and 56B.

On the spent bloom, the petals usually drop off cleanly.

In April in Visalia, Calif., blooms on the bush growing outdoors generally lasts about five to 7 days. Cut roses from plants grown outdoors and kept at normal indoor living temperatures generally last about 5 to 7 days.

Male Reproductive Organs

Stamens are many in number (average about 108) and are arranged regularly about the pistils; some are mixed with petaloids. The filaments are of short to medium length (about 0.05 to about 0.07 cm.), most with anthers. Filaments are between 2B and 5A at the base. The anthers are average for the class and all open approximately at the same time. Anther color is between 22A and 16A when immature and between 164B and 166A at maturity. Pollen is moderate.

Female Reproductive Organs

Pistils vary in number (average about 95). The styles are moderately even, average in length (about 0.4 to about 0.7 cm.), somewhat thin in caliper, and moderately separated to somewhat columnar. Stigma color is between 10C and 8C. Style color is near 4D. Ovaries are usually all enclosed in the calyx.

Foliage

The compound leaves are usually comprised of three to five or more leaflets and are borne abundantly. The five-leaflet leaves are about 13.5 to about 14.7 cm. in length and about 11.5 cm. in width at the widest point, moderately leathery to somewhat crisp in texture, and semi-glossy in finish. The terminal leaflets are about 5.7 to about 6.0 cm. in length and about 4.1 to about 4.6 cm. in width at the widest point, shaped oval to somewhat ovate with acute apices and moderately round to somewhat acute bases. Their margins are simply serrate.

The upper surface color of the mature leaf is between 137B and 137A. The under surface color of the mature leaf is between 138B and 139C. The upper surface color of the young leaf is between 137C and 138A. The under surface color of the young leaf is between 138B and 139C.

The rachis is average to somewhat medium in caliper and somewhat smooth. The upper side is moderately grooved with few hairs and stipitate glands on the edges of the grooves. The under side of the rachis is somewhat smooth with a very few stipitate glands and small prickles. The rachis color is between 146D and 146B.

The stipules are about 1.3 to about 1.5 cm. in length and of medium width (about 0.5 to about 1.0 cm.) with somewhat long straight points that usually turn out at an angle of more than 45 degrees and sometimes slightly recurve toward the stem. The stipules color is between 146D and 146B.

The petiole is about 4.0 to about 8.5 cm. in length and about 0.2 to about 0.3 cm. in diameter at the widest point. The petiole color is between 146D and 146B.

The plant displays an average degree of resistance to powdery mildew and rust as compared to other commercial varieties grown under comparable conditions in Visalia, Calif.

Growth

The plant has a compact medium height growing habit (about 85 to about 90 cm. in height and about 80 to about 90 cm. spread at the widest point), with full branching. It displays vigorous growth and the canes are of medium size caliper for the class.

The color of the major stems is between 146B and 146C. They bear some medium prickles that are about 0.05 to about 0.08 cm. in length. The large prickles are almost straight and angled slightly downward with a short length broad rounded base; prickle color is between 164A and 164C. The major stem bears some small prickles of similar shape and coloration.

The color of the branches is between 146B and 146C. They usually bear no large or small prickles. Sometimes they bear few large prickles which are of similar size and shape to the large prickles on the major stems; prickle color is between 187B and 183C.

The color of the new shoots is between 144A and 143C sometimes lightly suffused with between 182A and 182B. They bear no large or small prickles.

The following is claimed:

1. A new and distinct Floribunda rose plant, substantially as illustrated and described herein.

* * * * *